United States Patent
Noda et al.

(10) Patent No.: US 7,241,404 B2
(45) Date of Patent: Jul. 10, 2007

(54) RESIN COMPOSITION, OPTICAL FILTER AND PLASMA DISPLAY

(75) Inventors: Nobuhisa Noda, Hashima (JP); Takahiro Aoyama, Hyogo (JP)

(73) Assignee: Nippon Shokubai Co., Ltd, Osaka (JP)

( * ) Notice: Subject to any disclaimer, the term of this patent is extended or adjusted under 35 U.S.C. 154(b) by 270 days.

(21) Appl. No.: 10/822,114

(22) Filed: Apr. 9, 2004

(65) Prior Publication Data

US 2004/0204555 A1    Oct. 14, 2004

(30) Foreign Application Priority Data

Apr. 9, 2003    (JP) .............. 2003-105729

(51) Int. Cl.
  *F21V 9/04*    (2006.01)
  *G02B 5/22*    (2006.01)

(52) U.S. Cl. ............ 252/587; 252/588; 252/589; 359/361; 523/135

(58) Field of Classification Search ........ 252/587, 252/588, 589; 359/361; 523/135
See application file for complete search history.

(56) References Cited

U.S. PATENT DOCUMENTS

| | | | | |
|---|---|---|---|---|
| 5,278,243 | A | * | 1/1994 | Soane ............ 525/288 |
| 5,578,365 | A | * | 11/1996 | Kume et al. ........ 428/195.1 |
| 6,775,059 | B2 | * | 8/2004 | Kuwabara ........ 359/359 |
| 2002/0127395 | A1 | | 9/2002 | Kuwahara ........ 428/343 |
| 2002/0132122 | A1 | | 9/2002 | Marutsuka ........ 428/411.1 |
| 2003/0049456 | A1 | | 3/2003 | Kawasato et al. ..... 428/421 |
| 2003/0186040 | A1 | * | 10/2003 | Oya ............ 428/304.4 |
| 2003/0198805 | A9 | | 10/2003 | Sugimachi ........ 428/343 |

FOREIGN PATENT DOCUMENTS

| | | |
|---|---|---|
| JP | 2000-177064 | 6/2000 |
| JP | 2001-133624 | 5/2001 |
| JP | 2001-228323 | 8/2001 |
| JP | 2002-200711 | 7/2002 |
| JP | 3341741 | 8/2002 |
| JP | 2002-249721 | 9/2002 |
| JP | 2002-264278 | 9/2002 |
| JP | 2003-4939 | 1/2003 |
| JP | 2003-036033 | 2/2003 |
| JP | 2003-167119 | 6/2003 |
| JP | 2004-115718 | 4/2004 |

OTHER PUBLICATIONS

U.S. Appl. No. 10/638,430 corresponding to JP-A-2002-249721 (Japanese Patent Application No. 2001-051078).

* cited by examiner

*Primary Examiner*—D. S. Nakarani
(74) *Attorney, Agent, or Firm*—Occhiuti Rohlicek & Tsao LLP

(57) ABSTRACT

A resin composition which can enhance the heat resistance and the humidity resistance of a dye possessing the maximum absorption at wavelengths in the range of 380–780 nm is provided. It is obtained by polymerizing a monomer mixture containing 5–100 wt. % of a monomer represented by the formula: $CH_2=CR-COOX$ (wherein R denotes a hydrogen atom or a methyl group and X denotes a hydrocarbon group of 4–25 carbon atoms) and/or a fluorine atom-containing unsaturated monomer and containing a dye possessing the maximum absorption at wavelengths in the range of 380–780 nm in an acryl type resin having an acid value in the range of 0–30 mgKOH/g and a hydroxyl value in the range of 0–30 mgKOH/g.

12 Claims, No Drawings

RESIN COMPOSITION, OPTICAL FILTER AND PLASMA DISPLAY

BACKGROUND OF THE INVENTION

1. Field of the Invention

This invention relates to a resin composition excelling in heat resistance and moisture resistance and obtained by using an acrylic resin of a specific structure as a binder resin and adding thereto a dye possessing the largest absorption at wavelengths in the range of 380–780 nm and an optical filter and a plasma display both using the resin composition.

2. Description of the Related Art

In recent years, the PDP (plasma display panel) which enjoys a thin build and is adopted wide screens has been attracting attention. The PDP emits a near infrared ray during the course of plasma discharge. The fact that this near infrared ray induces such electrical apparatus as household TV sets, coolers, and video decks to malfunction has been posing a problem.

With a view to solving this problem, an invention which relates to a near infrared ray blocking film possessing high degrees of near infrared ray intercepting property and visible light transmitting property has been introduced (the JP-A-2001-133624). This patent document-discloses an infrared ray absorbing filter which has the difference between the largest and the smallest of transmittance and the largest transmittance in the near infrared ray region of wavelengths in the range of 850–1100 nm, the lowest transmittance in the visible region of wavelengths in the range of 450–650 nm, etc. set respectively in specific ranges. This invention purports that the infrared ray absorbing filter, when used in a plasma display, is enabled to absorb an unnecessary infrared ray radiated from the display and prevent the remote control using an infrared ray from malfunctioning by setting the difference between the largest and the smallest transmittance and the largest transmittance in the near infrared ray region of wavelengths in the range of 850–1,100 nm and, when installed in the front surface of the display, is enabled to secure brightness by setting the lowest transmittance in the visible region of wavelengths in the range of 450–650 nm. As infrared absorbing dyes, diimonium salt compounds, fluorine-containing phthalocyanine compounds, thionickel complex compounds, etc. are used. As binder resins, polyester type, acrylic type, and polyamide type resins have been disclosed.

In the meantime, a near infrared absorbing filter that an image is clarified by selectively absorbing the so-called neon orange light (in the region of 550–620 nm) liable to obscure the image as well as absorbing the near infrared ray for the purpose of preventing the conventional remote control device from malfunctioning without suffering the other visible light region to be substantially absorbed has been introduced (the JP-A-2002-200711). In the patent document, since the dye which is used for absorbing the neon orange light is deficient in weatherability and durability, a near infrared ray absorbing material which is obtained by having at least a transparent resin coating film containing a near infrared ray absorbing dye and a tackiness agent layer containing a dye capable of selectively absorbing wavelengths in the range of 550–620 nm superposed on a transparent substrate in an order allowing the tackiness agent layer to form the outermost layer is proposed. In the official gazette, the near infrared ray absorbing dye to be used is aimed at a dithiol nickel complex of a specific structure and a diimonium compound of a special structure, the dye capable of selectively absorbing the neon orange light (the region of wavelengths of 550–620 nm) is aimed at a cyanine dye of a specific structure, and the transparent resin is commended to be selected from among polyethylene terephthalate, polyethylene naphthalate, and polycycloolefins from the viewpoint of the stability of dye. The tackiness agent layer is obtained by dissolving the dye and the transparent resin mentioned above in an organic solvent and molding the resultant solution into a film with a roll coater. As the solvent, the use of 1,3-dioxolan or dichloromethane is mentioned.

As regards the optical filter to be disposed in front of the plasma display panel, an invention which is directed to using an optical filter incorporating therein a dye having the maximum absorption at wavelengths in the range of 570–600 nm for the purpose of absorbing such,wavelengths as degrade the color reproducibility in the proximity of the neon orange color that falls in the neighborhood of 590 nm has been disclosed (the JP-A-2001-228323). The patent document concerns the preparation of a PDP filter excellent in color reproducibility owing to the incorporation of a dye having the maximum absorption at wavelengths in the range of 570–600 nm in a transparent acrylic tackiness agent or a methacrylic resin with the object of improving the PDP in the emission spectrum and providing a PDP filter endowed with an enhanced color reproducibility.

A color adjusting filter which exhibits a sharp absorption in the regions of 480–520 nm and 550–610 nm of the light transmission curve and having an absorption in the wavelengths range of 380–420 nm without effecting the three primary colors, ie red, blue, and green has been also disclosed (the JP-A-2003-36033). In this official gazette, as a means to attain the absorption of the neon orange light, an effort to formulate the combination of a tetraazaborphyn type dye of a specific structure, a dipyrazoline type dye of a specific structure, a dipyrazolyl squalilium type dye of a specific structure, etc. and improve the color purity and the range of color reproduction is taught.

Further, a near infrared ray cutting material obtained by superposing on a transparent substrate a transparent resin coating film containing at least a near infrared absorption dye and a dye having the maximum absorption wavelengths in the range of 550–620 nm and consequently enabling the amount of the residual solvent in the transparent resin coating film to reach a level of not less than 5 wt. ppm and less than 500 wt. ppm has been introduced (the JP-A-2002-264278). It has been materialized in view of the fact that the molded article obtained by applying a composition having the near infrared ray absorbing dye mentioned above dispersed in a binder resin and drying the applied layer of the composition is at a disadvantage in revealing deficiency in the stability of the dye in the resin coating film, suffering the performance of near infrared ray absorption to decline and the color hue to change, and exhibiting inferior heat resistance. As concrete examples of the transparent resin to be used, polycarbonate and polyallylate are cited. As concrete examples of the near infrared absorbing dye, dithiol metal complex type, diimonium type, and phthalocyanine type dyes are cited. As concrete examples of the dye possessing the maximum absorption wavelengths in the range of 550–620 nm, cyanine type, squalium type, azomethine type, and xanthene type dyes are cited. As concrete examples of the solvent, THF, diethyl ether, and chloroform are mentioned.

Further, in view of the fact that when an infrared ray absorbing agent is contained in a polyurethane resin layer or other resin layer, the absorbing agent reveals deficiency in heat resistance and durability and suffers the effect of blocking the infrared ray to degrade with the elapse of time, an optical film containing as a main component a thermoplastic resin having a glass transition point in the range of 120–180° C. has been disclosed (the JP-A-2003-4939). It has a statement, reading in effect that if the glass transition point falls short of 120° C., the dye mixed therein will be deficient in durability and weatherability and the dye will be degraded by aging under the conditions of high temperature and high humidity. As concrete examples of the thermoplastic resin of this kind, polyester type resins, olefin type resins, cycloolefin type resins, and polycarbonate resins are cited. Then, as concrete examples of the color hue correcting agent which is capable of absorbing light of wavelengths in the range of 380–780 nm, azo type, condensed azo type, diimmonium type, phthalocyanine type, and anthraquinone type dyes are cited. As concrete examples of the near infrared ray abosorbing agent, polymethine type, phthalocyanine type, naphthalocyanine type, and metal complex type agents are cited. As the solvent for dissolving the main component, ketone type solvents such as cyclohexanone, ether type solvents, and ester type solvents such as butyl acetate, and ether alcohol type solvents such as ethyl cellosolve are enumerated as available.

The plasma display is required to use a near infrared ray absorbing agent capable of absorbing wavelengths of 850–1,100 nm for the purpose of preventing the remote control device from malfunctioning and is also required to absorb the so-called light of neon orange color emitted while the neon atom once excited is returned to the normal state. Since the conventional technique still falls short of absorbing this neon orange color fully sufficiently, the desirability of developing a technique which is capable of improving contrast has been finding popular approval.

Particularly, the dye which absorbs the neon orange light possibly reveals deficiency in heat resistance and humidity resistance and the deterioration of the dye possibly results in degrading the contrast along the course of time. Thus, the provision of an optical filter excelling in heat resistance and humidity resistance has been yearned for strongly.

SUMMARY OF THE INVENTION

The present inventors have studied dyes used in optical filters with the object of determining their stability and have consequently found that they have their stability affected by a binder layer serving to incorporate a given dye therein and that particularly a dye having the maximum absorption wavelengths in the visible region of 380–780 nm, when incorporated in a resin composition containing an acrylic type resin having a specific amount of a polar group, exhibits markedly enhanced heat resistance and humidity resistance. This invention has been perfected as a result. When the specific acrylic type resin mentioned above is used as a binder, the effects of the drying conditions on the performance of the dye are small. Thus, the range of solvents eligible for adoption is copiously widened because even high boiling solvents heretofore rated as unusable by reason of boiling points during the course of drying become usable. Further, the decrease attained in the effect of the amount of residual solvent in the coating film results in facilitating the management of drying conditions, greatly curtailing the conventional drying time, prominently enhancing productivity, and promoting a large cost down.

According to this invention, by using the acrylic type resin of a specific structure as the binder resin, it is made possible to retain stably a dye which possesses the maximum absorption at wavelengths in the range of 380–780 nm. Particularly, since the resin excels in heat resistance and humidity resistance, the use of this resin prevents the dye mentioned above from being degraded, effects the absorption of the neon orange light emitted in the PDP, and clarifies the contrast.

Even when the acrylic type resin mentioned above is diluted with a high boiling solvent, it can not impair the stability of the dye contained in the dried coating film. Thus, the range of solvents eligible for choice in the production of an optical filter can be widened.

The acrylic type resin to be used in this invention is enabled to have the long-term resistance thereof to heat and humidity exalted by causing the monomer components thereof to include an ultraviolet light-absorbing monomer and an oxidation preventing monomer further.

DESCRIPTION OF THE PREFERRED EMBODIMENT

The first aspect of this invention is directed toward a resin composition comprises an acryl type resin obtained by polymerizing a monomer mixture containing 5–100 wt. % of a monomer represented by the following formula (1) and/or a fluorine atom-containing unsaturated monomer and having an acid value in the range of 0–30 mgKOH/g and a hydroxyl value in the range of 0–30 mgKOH/g, and a dye having the maximum absorption at wavelengths in the range of 380–780 nm.

$$CH_2=CR-COOX \qquad (1)$$

(wherein R denotes a hydrogen atom or a methyl group and X denotes a hydrocarbon group of 4 to 25 carbon atoms.)

When the dye possessing the maximum absorption at wavelengths of 380–780 nm and used in the optical filter for the purpose of absorbing the neon orange light was studied for stability, it was found to excel in the stability on the condition that a resin of a specific structure was used as a binder resin. As the resin which answers this description, the acrylic type resin which essentially contains a monomer represented by the formula (1) shown above and/or a fluorine atom-containing unsaturated monomer is available.

As concrete examples of the hydrocarbon groups of 4–25 carbon atoms denoted by X in the formula (1) above, alicyclic hydrocarbon groups such as cyclohexyl group, methyl cyclohexyl group, and cyclododecyl group; straight chain or branched chain alkyl groups such as butyl group, isobutyl group, tert-butyl group, 2-ethylhexyl group, heptyl group, octyl group, nonyl group, decyl group, undecyl group, dodecyl group, pentadecyl group, and octadecyl group; and polycyclic hydrocarbon groups such as bornyl group and isobornyl group may be cited. Among other hydrocarbon groups enumerated above, alicyclic hydrocarbon groups, branched chain alkyl groups, straight chain alkyl groups having 6 or more carbon atoms, and polycycloic hydrocarbon groups prove favorable and alicyclic hydrocarbon groups having not less than six carbon atoms and polycyclic hydrocarbon groups prove more favorable.

As concrete examples of the monomer represented by the formula (1) mentioned above, cyclohexyl (meth)acrylate, methylcyclohexyl (meth)acrylate, cyclododecyl (meth)acrylate, tert-butyl cyclohexyl (meth)acrylate, isobutyl (meth) acrylate, tert-butyl (meth)acrylate, lauryl (meth)acrylate, isobornyl (meth)acrylate, stearyl (meth)acrylate, 2-ethylhexyl (meth)acrylate, and such cyclohexyl alkyl esters of (meth)acrylic acid as disclosed in the JP-A-2002-69130 may be cited. In this invention, the monomers represented by the formula (1) mentioned above may be used either singly or in the form of a combination of two or more members.

As concrete examples of the fluorine atom-containing unsaturated monomer, radically polymerizing monomers possessing a perfluoroalkyl group or a perfluoroether group may be cited. As perfluoroalkyl groups, perfluoromethyl group, perfluoroethyl group, perfluoropropyl group, perfluorobutyl group, perfluorohexyl group, perfluorooctyl group, perfluorodecyl group, perfluorododecyl group, and perfluorotetradecyl group prove suitable.

As such fluorine atom-containing unsaturated monomers, $CH_2=C(CH_3)COOCH_2(CF_2)_4CF_3$, $CH_2=C(CH_3)COOCH_2CH_2(CF_2)_6CF_3$, $CH_2=CHCOO(CF_2)_6CF_3$, $CH_2=CHCOOCH_2CH_2(CF_2)_7CF_3$, $CH_2=CHCOOCH_2CH_2(CF_2)_5CF(CF_3)_2$, $CH_2=C(CH_3)COOCH(OCOCH_3)CH_2(CF_2)_6CF(CF_3)_2$, $CH_2=CHCOOCH_2CH(OH)CH_2(CF_2)_6CF(CF_3)_2$, $CH_2=CHCOOCH_2CH_2(CF_2)_8CF_3$, $CH_2=C(CH_3)COOCH_2CH_2NHCO(CF_2)_8CF_3$, $CH_2=CHOCONHCO(CF_2)_7CF(CF_2Cl)CF_3$, $CH_2=CHCOOCH_2CH_2N(C_3H_7)SO_2(CF_2)_7CF_3$, $CH_2=CHCOOCH_2CH_2CH_2CH_2(CF_2)_7CF_3$, $CH_2=C(CH_3)COOCH_2CH_2N(C_2H_5)SO_2(CF_2)_7CF_3$. $CH_2=CHCOOCH_2CH_2NHCO(CF_2)_7CF_3$, $CH_2=CHCOO(CH_2)_3(CF_2)_6CF(CF_3)_2$, $CH_2=CHCOOCH_2(CF_2)_{10}H$, $CH_2=C(CH_3)COOCH_2(CF_2)_{10}CF_2Cl$, $CH_2=CHCONHCH_2CH_2OCOCF(CF_3)OC_3F_7$, and $CH_2=CHCONHCH_2CH_2OCOCF(CF_3)(OC_3F_6)_2OC_3F_7$ are suitable. These monomers may be used either singly or in the form of a combination of two or more members. The fluorine atom-containing unsaturated monomers which are commercially available are also usable. The products of Kyoeisha Chemical CO., LTD. sold under such trademark designations as "Light Ester FM-108," "Light Ester M-3F," and "Light Ester M-4F" and the products of Nihon Mectron CO., LTD. sold under such trademark designations as "CHEMINOX FAAC," "CHEMINOX FAMAC," "CHEMINOX FAAC-M," "CHEMINOX FAMAC-M," "CHEMINOX PFAE," and "CHEMINOX PFOE" are examples.

As regards the amount of the monomer of the formula (1) mentioned above and/or the amount of the fluorine atom-containing unsaturated monomer mentioned above, the amount of the monomer represented by the formula (1) mentioned above or the fluorine atom-containing unsaturated monomer mentioned above when used alone or the total amount of the monomer represented by the formula (1) mentioned above and the fluorine atom-containing unsaturated monomer mentioned above when used together as contained in arbitrary ranges falls in the range of 5–100 wt. %, preferably 10–90 wt. %, and more preferably 15–80 wt. %, based on the amount of the total monomer forming the acrylic type resin, for example, taken as 100 wt. %. If this amount falls short of 5 wt. %, the shortage will result in degrading the dye in heat resistance and humidity resistance along the course of time even when the monomer is made to add the dye. This is because the coating film containing the acrylic type resin obtained by copolymerizing the monomer represented by the formula (1) mentioned above and the fluorine atom-containing unsaturated monomer acquires low hygroscopicity and prevents the coating film from admitting the moisture which forms a cause of the deterioration of the dye.

The other copolymerizable unsaturated monomers which are usable other than the monomers mentioned above include carboxyl group-containing unsaturated monomers such as (meth)acrylic acid, itaconic acid, and maleic anhydride; acidic phosphoric ester type unsaturated monomers such as 2-(meth)acryloyloxyethyl acid phosphate; unsaturated monomers possessing an active hydrogen-containing group such as 2-hydroxyethyl (meth)acrylate, hydroxypropyl (meth)acrylate, hydroxybutyl (meth)acrylate, and caprolactone-modified hydroxy (meth)acrylate (such as the product of Dicel Chemical Industries, LTD. and sold under the trademark designation of "Praccel FM"); (meth)acrylic esters such as methyl (meth)acrylate, ethyl (meth)acrylate, propyl (meth)acrylate, isopropyl (meth)acrylate, and butyl (meth) acrylate; and unsaturated monomers containing an epoxy group such as glycidyl (meth)acrylate, for example.

Further, nitrogen atom-containing unsaturated monomers such as (meth)acryl amide, N,N'-dimethylaminoethyl (meth)acrylate, N,N-diethylaminoethyl (meth)acrylate, imide (meth)acrylate, and cyclohexylmaleimide; unsaturated monomers containing not less than two polymerizable double bonds such as ethylene glycol di(meth) acrylate, triethylene glycol di(meth)acrylate, tripropylene glycol di(meth) acrylate, trimethylol propane tri(meth)acrylate, and pentaerythritol tetra(meth)acrylate; halogen atom-containing unsaturated monomers such as vinyl chloride (excluding the fluorine atom-containing unsaturated monomers mentioned above); aromatic unsaturated monomers such as styrene and α-methyl styrene; vinyl esters such as vinyl acetate; and vinyl ethers are also usable.

When the dye requires further improvement in durability, it suffices to use an unsaturated monomer containing an ultraviolet light-absorbing group (polymerizing ultraviolet light-absorbing monomer) such as a benzotriazole type, benzophenone type, or triazine type monomer. To be specific, the product of Otsuka Chemicals CO., LTD. sold under the trademark designation of "RUVA 93" and the product of Osaka Yuki Kagaku K.K. sold under the trademark designation of "BP-1A" may be cited as concrete examples. They may be used either singly or in the form of a combination of two or more members. The products of Asahi Denka Kogyo K.K. sold under the trademark designations of "Adekastab LA-82" and "Adekastab LA-87" may be cited as concrete examples of the unsaturated monomer containing an ultraviolet stabilizer group (polymerizing ultraviolet stabilizer monomer) and the product of Sumitomo Chemicals CO., LTD. sold under the trademark designations of "Sumilizer GS" and "Sumilizer GM" as concrete examples of the unsaturated monomer possessing ability to prevent oxidation. They may be used either singly or, when necessary, in the form of a combination of two or more members. By incorporating a quencher in the composition of theresin of this invention, it is made possible to enhance further the durability of the dye. As concrete examples of the quencher of this sort, the products of Nippon Carlit Co., Ltd. sold under the trademark designations of "CIR1080," "CIR1081," and "CIR960," the product of Midori Kagaku K.K. sold under the trademark designation of "MIR101," and the product of Sumitomo Seika Chemicals CO., LTD. sold under the trademark designation of "EST5" may be cited.

In this invention, the total amount of the polymerizing ultraviolet light-absorbing monomer, the polymerizing ultraviolet light stabilizer monomer, and the polymerizing oxidation preventing monomer to be incorporated in the composition is properly selected in the range of 0–50 wt. %, based on the amount of the total monomer. The kinds and the amounts of the component monomers to be used must be adjusted so that the produced acrylic type resin assume an acid value in the range of 0–30 mgKOH/g and a hydroxyl value in the range of 0–30 mgKOH/g. The acid value is indicated by the number of mg of potassium hydroxide necessary for neutralizing the carboxyl group contained in 1 g of an acrylic type resin and reported by the unit of mgKOH/g. The hydroxyl value is indicated by the number of mg of potassium hydroxide necessary for neutralizing the acetic acid required for acetylating the hydroxyl group contained in 1 g of the acrylic type resin. Thus, the amounts of the carboxyl group and the hydroxyl group contained in a given monomer to be incorporated are measured to determine whether they fall in the aforementioned ranges of acid value and hydroxyl value.

The method of polymerization for the production of the acrylic type resin can be carried out by any of the heretofore known methods of polymerization such as, for example, solution polymerization, dispersion polymerization, suspension polymerization, and emulsion polymerization using a polymerization initiator. The solvent to be used in the solution polymerization does not need to be particularly restricted. As concrete examples of the solution, alcohols such as iso-propanol, n-butanol, and diacetone alcohol; cellosolves such as ethyl cellosolve, butyl cellosolve, and ethyl cellosolve acetate; propylene glycols such as propylene glycol monomethyl ether, propylene glycol monoethyl ether, and propylene glycol monoethyl ether acetate; ketones such as acetone, methylethyl ketone, cyclohexanone, and methyl isobutyl ketone; ethers such as tetrahydrofuran; esters such as butyl acetate, ethyl butyrate, and vinyl butylate; halogenated hydrocarbons such as methylene chloride; aromatic hydrocarbons such as toluene and xylene; and high polarlity solvents such as dimethyl acetamide and N-methyl pyrrolidone may be cited. These solutions may be used either singly or in the form of a combination of two or more members. The amount of the solvent to be used may be properly selected in accordance with such factors as the conditions of polymerization and the proportions by weight of the component polymers in the binder resin.

The polymerization initiator mentioned above does not need to be particularly restricted but may be selected from among ordinary radical polymerization initiators such as, for example, 2,2'-azobis-(2-methybutylonitrile), tert-butylperoxy-2-ethylhexanoate, 2,2'-azobisisobutylonitrile, benzoyl peroxide, and di-tert-butyl peroxide. These solvents may be used either singly or in the form of a combination of two or more members. Though the amount of the polymerization initiator to be used may be properly set by the physical constants of the polymer expected to be obtained, it is preferred to fall in the range of 0.01–50 wt. %, and more preferred to fall in the range of 0.05–20 wt. %, based on the total amount of the monomer component taken as 100 wt. %.

The polymerization conditions in the polymerization method mentioned above do not need to be particularly restricted but may be properly set based on the method of polymerization. The polymerization temperature, for example, is properly set in the range of room temperature –200° C. and more properly in the range of 40–140° C. The polymerization time may be properly set, depending on the composition of monomer components and the kind of the polymerization initiator so as to enable the polymerization reaction to complete.

The acrylic type resin of this invention has an acid value in the range of 0–30 mgKOH/g, more preferably in the range of 0–20 mgKOH/g, and particularly preferably in the range of 0–15 mgKOH/g and a hydroxyl value in the range of 0–30 mgKOH/g, more preferably in the range of 0–20 mgKOH/g, and particularly preferably in the range of 0–15 mgKOH/g. If the acid value exceeds 30 mgKOH/g, the excess will possibly degrade the optical filter in humidity resistance and heat resistance and, when a transparent substrate is superposed with the resin composition of this invention for the purpose of forming an optical filter, will possibly degrade the adhesive property of the resin composition after the test for humidity resistance. By the same token, if the hydroxyl value exceeds 30 mgKOH/g, the excess will possibly degrade the dye in humidity resistance and heat resistance and possibly degrade the adhesive property with the transparent substrate layer after the test for humidity resistance. When the acid value and the hydroxyl value fall in the ranges mentioned above, the incorporation of the dye which will be described herein below serves to preclude the dye from yielding to deterioration by aging due to the residual solvent by the mechanism yet to be elucidated. This advantage may be ascribed to the fact that the molecule of the dye is stabilized by the specific structure represented by the above mentioned formula (1) and/or fluorine atom-containing unsaturated monomer of the acrylic type resin which is the matrix of the dye and the presence of the specific amount of the polar group. A low boiling solvent has been heretofore used for facilitating the removal of the solvent. Since this invention incurs only a nominal deterioration of the coloring material by the residual solvent, it is allowed to use a high boiling solvent and widen the range of solvents to be selected.

The acrylic type resin to be used in this invention is preferred to have a weight average molecular weight in the range of 3,000–1,000,000, more preferably in the range of 5,000–700,000, and particularly preferably in the range of 7,000–500,000. If the molecular weight falls short of 3,000, the shortage will possibly lowering the adhesive property with the substrate after the test for humidity resistance. Conversely, if it exceeds 1,000,000, the excess will possibly lower the workability of coating and degrade the wettability with the transparent substrate and lowering the adhesive property after the test for humidity resistance. The weight average molecular weight is measured by the gel permeation chromatography (GPC) and returned to polystyrene.

The glass transition point of the acrylic type resin to be used in this invention is preferred to be in the range of –50–200° C. and more preferably in the range of –30–180° C. If it falls short of –50° C., the shortage will possibly lower the dye in humidity resistance and heat resistance and degrade the adhesive property with the transparent substrate after the test for humidity resistance. If the glass transition point exceeds 200° C., the excess will be at a disadvantage in terms of the workability of coating.

As the dyes possessing the maximum absorption wavelengths in the visible range of 380–780 nm and incorporated in the acrylic type resin mentioned above, such cyanine dyes represented by the formulas (6), (7), and (8) described in the JP-A-2002-200711, such tetraazaporphyrin type dyes represented by the general formula (I) disclosed in the JP-A-2003-36033, such dipyrazolyl methine type dyes represented by the general formula (II), such dipyrazolyl squalilium type dyes represented by the general formula (III), and such other heretofore known dyes as cyanine type, azulenium type, squalilium type, diphenyl methane type, triphenyl methane type, oxazine type, azine type, thiopyrilium type, viologen type, azo type, azo metal complex salt type, bisazo type, anthraquinone type, perylene type, indanthrone type, nitroso type, metal thiol complex type, indigo type, azomethyne type, xanthene type, oxanol type, indoaniline type, and quinoline type are widely usable. As concrete examples of commercially available dyes, the products of Asahi Denka Kogyo K.K. sold under the trademark designations of "Adeka Acruse TW-1367," "Adeka Acrute SG-1574," "Adeka AcruseTW1317," "Adeca Acruse FD-3351," and "Adeka Acruse Y944" and the products of Hayashibara Seibutsu Kagaku Kenkyusho sold under the trademark designation of "NK-5451," "NK-5532," and "NK-5450" may be cited. This invention is particularly suitable for the dipyrazolyl squalilium type dye and the tetraazaporphyrin type dye shown by the following formulas.

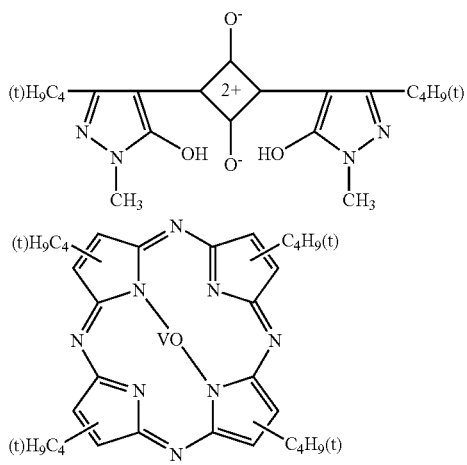

The resin composition of this invention results from adding the acrylic type resin mentioned above and a dye having the maximum absorption at wavelengths in the ranges of 380–780 nm together. This resin composition may be prepared uniformly by dissolving or dispersing the dye in advance in a solvent and kneading the solution or dispersion with the acrylic type resin. Otherwise, the resin composition may be uniformly prepared by dissolving the acrylic type resin and kneading the solution and the dye. Further, the reaction solution formed during the polymerization may be used in its unmodified form as the acrylic type resin-containing solution.

The amount of the acrylic type resin to be incorporated in the resin composition of this invention properly falls in the range of 50–99.9995 wt. %, more properly in the range of 60–99.9985 wt. %, and particularly properly in the range of 70–99.9985 wt. %, based on 100 wt. % of the resin composition as reduced to involatile form. If this amount falls short of 50 wt. %, the shortage will possibly prevent the visible light absorbing coating film formed from the resin composition from acquiring satisfactory solid state properties. If the amount exceeds 99.9995 wt. %, the excess will possibly prevent: the performance of the visible light absorption from being enhanced satisfactorily.

Meanwhile, the amount of the dye to be incorporated in the resin composition properly falls in the range of 0.0005–20 wt. % and more properly in the range of 0.0015–10 wt. %, based on 100 wt. % of the resin composition as reduced to aninvolatile form. If this amount falls short of 0.0005 wt. %, the shortage will possible prevent the visible light absorbing coating film formed from the resin composition from acquiring fully satisfactory performance of visible light absorption. If the amount exceeds 20 wt. %, the excess will possiblyprevent the visible light absorbing coating film from acquiring fully satisfactory solid phase properties.

Further, the resin composition of this invention, when necessary, may incorporate therein one or more solvents, additives, or curing agents without sacrificing the performance. As the solvents, the same organic solvents as mentioned above may be cited. When the transparent substrate is polycarbonate which is vulnerable to an aromatic solvent, for example, use of an aliphatic alcohol type solvent proves advantageous. As concrete examples of the aliphatic alcohol type solvent, isopropyl alcohol, n-butyl alcohol, propylene glycol monomethyl ether, etc. may be cited. These solvents may be used either singly or in the form of a combination of two or more members. As the additives, the heretofore known additives in popular use in the resin composition for forming a film or a coating film may be used. As concrete examples of the additives, dispersant; leveling agent; inorganic fine powders such as colloidal silica and alumina sol, defoaming agent, anti-sagging agent, silane coupling agent, white titanium pigment, pigments such as compound oxide pigment, carbon black, organic pigment, and pigment intermediate; antioxidant; viscosity enhancer; ultraviolet light stabilizer; metal inactivating agent; peroxide decomposing agent; filler, reinforcing agent; plasticizer; lubricant; corrosion-proofing agent, anti-rust agent; fluorescent brightening agent; organic and inorganic ultraviolet light absorber; inorganic heat ray absorber; organic and inorganic fire righting agent; and antistatic agent may be cited. As the curing agent, polyisocyanate compound or a modified product thereof and such gardening agents as epoxy resin and aminoplast resin may be used.

The resin composition of this invention may be used as films and sheets for optical, agricultural, architectural, vehicular, and image recording fields, freezer and cold storage showcases, pigment intensifying solar cells and other solar cells, photosensitive materials using a semiconductor laser light as a light source, information recoeving materials such as optical discs, materials for preventing eyes from fatigue, photothermal conversion materials such as sensitive papers, and adhesive agents. It is particularly suitable for use as films and sheets for optical and image recording devices, information recording materials for optical discs, photothermal conversion maerials such as sensitive papers, and tackifier materials.

The second aspect of this invention is directed toward an optical filter superposing a layer formed of the resin composition set forth in claim 1 on a transparent substrate layer. Consequently, an optical filter which excels in the ability to absorb the neon orange light, manifests excellent heat resistance and humidity, and secures stable absorbing efficiency for a long time can be obtained. It is advantageous, for example, to prepare a solution or a dispersion of the resin composition in a proper solvent, applying the solution or dispersion on a transparent substrate layer in the form of a sheet or a film by a known method of application, and drying the applied layer thereby superposing on the transparent substrate layer the dye-containing resin layer formed of a binder resin containing the dye and completing a laminate.

The transparent substrate to be used in this invention does not need to be particularly restricted but is only required to be made of a material substantially transparent and incapable of inducing heavy absorption or dispersion. As concrete examples of the transparent substrate, glass, polyolefin type resin, amorphous polyolefin type resin, polyester type resin, polycarbonate type resin, acryl type resin, polystyrene type resin, polyvinyl chloride type resin, polyvinyl acetate type resin, polyarylate type resin, and polyether sulfone type resin may be cited. Among other transparent substrates enumerated above, amorphous polyolefin resin, polyester resin, polycarbonate resin, acrylic type resin, polyarylate resin, and polyether sulfone resin prove particularly advantageoues. Further, the transpaent substrate mentioned above may be given a surface treatment by such known methods as corona discharge treatment, flame treatment, plasma treatment, glow discharge treatment, surface coarsening treatment, and chemical treatment or may be coated with an anchor coating material or a primer coating material.

The transparent substrate material resin mentioned above may incorporate such known additives as heat-resistant anti-aging agent, slidant, and antistatic agent. It is molded in the form of a film or a sheet by such known methods as injection molding, T-die molding, calendar molding, and compression molding or by a method which comprises dissolving the resin in an organic solvent and casting the resultant solution. The substance which forms the transparent substrate may be in an unstretched form, in a stretched form, or in a form laminated with other substrate.

The following methods (1)–(4) are available for the manufacture of the optical filter of this invention.

(1) The resin composition and any of the organic solvents selected properly are added together to lower the viscosity of the composition and the resultant mixture is applied to the transparent substrate layer and then dried. (2) In accordance with the molding method proper for thermoplastic resin, the resin composition is fused, then molded into a film or sheet by extrusion molding, injection molding, or compression molding, and extrusion molding, and joined to the transparent substrate with an adhesive agent. (3) The resin composition is fused, extruded in the form of a film or a sheet, and superposed on the transparent substrate by the technique of extrusion laminating. (4) The resin composition is fused and coextruded together with the transparent substrate. The manufacture of the sheet or film as a single layer may be accomplished by (1) a method which comprises solving or dispersing the resin composition with a proper solvent, casing the solution or dispersion onto a carrier, and drying the cast sheet or film or (2) a method which comprises fusing the resin composition and molding the fused resin composition into a film or a sheet by extrusion molding, injection molding, or compression molding by following the ordinary molding technique proper for a thermoplastic resin. As concrete examples of the method for applying the resin composition to the transparent substrate, immersion, spraying, brushing, curtain flow coating, gravure coating, roll coating, spin coating, blade coating, bar coating, reverse coating, die coating, spray coating, and electrostatic coating may be cited.

The thickness of the resin composition layer in this invention does not need to be particularly restricted but may be properly set, depending on such factors as the purpose of application. This thickness is preferred to be such that the applied layer, when dried, reaches a thickness in the range of 0.5–1,000 μm, preferably 1–100 μm.

As the tackiness agent layer which can be used for superposing the transparent substrate layer and the resin composition layer, such known adhesive agents as the urethane type, acryl type, and silicone type adhesive agent are available. The thickness of the tackiness agent layer falls in the range of 1–200 μm, and preferably in the range of 3–100 μm. The tackiness agent layer may contain such additives as ultraviolet light absorbing agent and ultraviolet light stabilizer. The use of the adhesive layer results in strengthening the adhesion between the resin composition layer and the transparent substrate layer and rendering separation and deterioration difficult to proceed between the resin composition layer and the transparent substrate material.

The optical filter of this invention may be furnished further with a near infrared absorption layer, an electromagnetic wave blocking layer, a light reflection preventing layer, a non-glare layer, and a scratch-proofing layer. Though these component layers in the filter may be superposed in any arbitrarily selected order, they are preferred to be superposed in the order mentioned above. The thickness of each layer generally falls in the range of 0.1–30 μm and satisfactorily in the range of 0.5–10 μm.

The near infrared ray absorbing layer may have a dye having the maximum absorption at wavelengths in the range of 780–1,200 nm contained in the resin composition mentioned above to effect the maximum absorption at wavelengths in the range of 380–780 nm and function as a near infrared ray absorbing layer as well. Alternatively, such near infrared ray absorbing layers maybe used between the component layers of a filter produced by using a near infrared ray absorbing agent as a laminating component. For example, the near infrared ray absorbing layer may be formed as added to any of the filter component layers such as the adhesive agent layer to be described herein below or the scratch preventing layer to be described herein below or to the layers formed of an anchor coating agent to be used properly.

As concrete examples of the near infrared ray absorbing agent, phthalocyanine compounds represented by the formula (1) in the JP-A-2001-106689, aromatic dithiol type metal complexes represented by the general formula (1) described in the JP-A-2002-82219, aromataic diimmonium compounds represented by the general formulas (2) and (3), aromatic diol compounds represented by the general formulas (4)–(9), diimmonium type compounds described in the JP-A-2001-133624, and nitroso type compounds and metal complex salts thereof, cyanine type compounds, thiol nickel complex salt type compounds, dithiol nickel complex salt type compounds, aminothiol nickel complex salt type compounds, phthalocyanine type compounds, naphthalocyanine type compounds, triallyl methane type compounds, immonium type compounds, diimmonium type compounds, naphthoquinone type compounds, anthraquinone type compounds, amino compounds, amminium salt type compounds, such organic substances as squalilium type compounds and methine type compounds, antimony-doped tin oxide, and indium-doped tin oxide may be cited. The dye may be incorporated together with a dye possessing the maximum absorption at wavelengths in the range of 380–780 nm into the acrylic type resin as described above. It may be otherwise incorporated in the acryl type resin or other transparent resin and processed into a near infrared ray absorbing layer by using the heretofore known technique. When a separate near infrared ray absorbing layer is to be formed, the transparent substrate layer of this invention, the resin composition layer mentioned above, and an optionally incorporated adhesive layer may be superposed in any order. Since the optical filter of this invention contains a dye having the maximum absorption at wavelengths in the range of 380–780 nm and possesses a layer containing a dye possessing the maximum absorption at wavelengths in the range of 780–1,200 nm, it can precluding the remote control unit from malfunctioning, exhibits an excellent ability to absorb the neon orange light, and proves very useful.

The electromagnetic wave blocking layer is installed for the purpose of preventing the electromagnetic waves generated in consequence of the mission of light from the display device from exerting adverse effects on the human body and on the electronic devices. The electromagnetic wave blocking layer is formed of a thin film of such metal or metal oxide as silver, copper, indium oxide, zinc oxide, indium tin oxide, and antimony tin oxide. It can be manufactured by utilizing such heretofore known dry plating technique as vacuum evaporation, ion plating, sputtering, CVD, and plasma chemical vacuum evaporation. The most popularly used of all the electromagnetic wave blocking layer is the thin film of indium tin oxide (hereinafter occasionally abbreviated as "ITO") The thin film of copper furnished with holes in the form of a mesh and the laminate obtained by alternately superposing dielectric layers and metal layers may be properly used. The dielectric layer generally has a transparent metal oxide such as indium oxide or zinc oxide and a metal layer of silver or silver-palladium alloy. The laminate generally has an odd number, in the approximate range of 3–13, of component layers starting from a dielectric layer. The electromagnetic wave blocking layer may be formed in its unmodified form on any of the component layers of the filter for the display mentioned above or may be formed on a resin film or glass by vacuum evaporation of sputtering and thereafter combined with the filter.

The reflection preventing layer is intended to repress reflection on the surface and prevent the external light of the fluorescent lamp from finding access to the surface. The reflection preventing layer in one version comprises a thin film of metal oxide or an inorganic substance such as fluoride, silicide, boride, carbide, nitride, or sulfide and in the other version results from having such resins as acryl resin and fluorine resin which have different indices of refraction spread in one layer or superposed in many layers. In the former case, the use of the same dry plating technique as cited in the paragraph dealing with the electromagnetic blocking layer, ie a method of forming the reflection preventing layer in the form of a single layer or in the laminated form in its unmodified form on the layer of the filter for the display mentioned above and thereafter joining it to the filter and a method of forming the layer by vacuum evaporation or sputtering on a resin film or glass and joining it to the filter may be cited. In the latter case, a molding technique common to resin laminate such as a method of joining a film or a sheet made of such resin as acryl resin or fluorine resin to a filter for the display by the use of an adhesive agent may be cited. Besides these methods, a technique of giving a film a treatment for prevention of reflection and applying the film to the filter by adhesion may be adopted.

The nonglare layer is formed by transforming fine powder of silica, melamine resin, or acryl resin into an ink, applying the resultant ink to any of the filters of this invention by the known coating method, and aging or photosetting the applied layer of ink. Otherwise, a film which has undergone a nonglare treatment may be applied to the filter by adhesion. Then, the scratch-proofing layer is formed by dissolving or dispersing acrylate such as urethane acrylate, epoxy acrylate, or polyfunctional acrylate and a photopolymerization initiator in an organic solvent, applying the resultant coating solution by the heretofore known method to any of the component layers of the filter of this invention, preferably to the outermost component layer, drying the applied layer of the coating solution, and photosetting the dried layer.

The optical filter of this invention is properly a laminate having the transparent substrate and the resin composition layer as the basic component layers and optionally comprising the near infrared ray absorbing layer, the electromagnetic blocking layer, the light reflection preventing layer, the nonglare layer, and the scratch-proofing layer. Optionally, it maybe further furnished with an antioxidant layer and an untraviolet light absorber-containing layer. The order in which the component layers are superposed does not need to be particularly restricted and the method of lamination does not need to be particularly restricted. Generally, the component layers are superposed as interposed by transparent substrate material and then joined together with an adhesive layer to complete a laminate. In this case, the surface treatment such as corona discharge treatment, glow discharge treatment, plasma treatment, flame treatment, or treatment with a chemical agent and the use of such known anchor coating agents as isocyanate type, polyester type, polyethylene imine type, polybutadiene type, and alkyl titanate bring the advantage of enhancing the adhesiveness during the course of adhesion and enabling the adhesive agent to be applied evenly.

The third aspect of this invention is directed toward a plasma display using the optical filter mentioned above. The optical filter may be provided on the outermost layer thereof with a tackifier agent layer serving to join the filter to the surface of the display. Owing to the tackiness agent layer, the filter can be joined easily and conveniently by adhesion to the front surface of the display either during the course of the production of the display or after the production of the display. Heretofore, the near infrared ray absorbing filter, the electromagnetic wave blocking filer, etc. must be disposed in front of the display itself. The filter of this invention has only to be applied by adhesion to the display. Thus, it not merely simplifies the process of production but also permits a decrease of the wall thickness of the display system as a whole because the filter and the display are integrally formed.

As concrete examples of the tackiness agent which forms the tackiness agent layer, rubbers such as styrene butadiene rubber, polyisoprene rubber, polyisobutylene rubber, natural rubber, neoprene rubber, chloroprene rubber, and butyl rubber and polyalkyl acrylates such as polymethyl acrylate, polyethyl acrylate, and polybutyl acrylate may be cited. These rubbers may be used either singly or in the form of a combination of two or more members. Optionally, it may further incorporate therein such a tackiness imparting agent as pickolite, polybale, or rosin ester.

The method for forming the tackiness agent layer specifically comprises dispersing or dissolving the rubber or the polyalkyl acrylate mentioned above in one solvent or a plurality of solvents selected from the group consisting of halogen type, alcohol type, ketone type, ester type, ether type, aliphatic hydrocarbon type, and aromatic hydrocarbon type thereby adjusting the viscosity thereof, applying the resultant solution or dispersion by such known coating techniques as dipping, flow coating, spraying, bar coating, gravure coating, roll coating, blade coating, or air knife coating, and then drying the solvent in the applied layer to complete a tackiness agent layer.

The thickness of the tackiness agent layer generally falls in the range of 5–100 µm and preferably in the range of 10–50 µm. It is commendable to provide the tackiness agent layer on the surface thereof with a release film capable of keeping dust from adhering to the tackiness agent layer and then keep the tackiness agent layer protected with the release film till the tackiness agent layer is joined by adhesion to the surface of the plasma display. In this case, the work of joining by adhesion can be facilitated by forming a part not provided with the tackiness agent layer or interposing a nonadhesive film between the tackiness agent layer and the release film in the edge part of the filter.

If an air bubble enters between the surface of the plasma display and the filter during the adhesion of the filter to the plasma display, it will entail a serious practical problem of deforming an image or preventing the screen from showing a clear view of image. Due precautions, therefore, should be taken to avoid such accidental entry of air bubbles. The plasma display of this invention can be manufactured by mounting the optical filter of this invention directly on the surface of the display as described above or by preparatorily joining the optical filter to a transparent glass or transparent resin sheet and then mounting the optical filter of this invention on the surface of the display.

Incidentally, the resin composition and the optical filter of this invention can be used for such flat-face type display devices as liquid crystal display device (LCD), electroluminescence display (EL), plasma address liquid crystal (PALC) display, and field emission display (FED) and such display devices as cathode tube display device (CRT) as well as for the plasma display. In this case, they may be installed on the visible range side of the display device or they may be separated from the display device. Otherwise, they may be directly mounted on the surface of the display device.

EXPERIMENT

Now, this invention will be described more specifically below with reference to working examples.

SYNTHESIS EXAMPLE 1

A 500-ml flask provided with a stirrer, a dropping orifice, a thermometer, a cooling pipe, and a nitrogen gas inlet port was charged with 30 g of ethyl acetate. Further, a dropping tank was charged with a monomer mixture consisting of 10 g of cyclohexyl methacrylate, 90 g of methyl methacrylate, and 0.5 g of tert-butyl-peroxy-2-ethylhexanoate. The flask, after admitting 20 wt. % of the mixture, was heated to a refluxing temperature. After the temperature elevation, the remaining 80 wt. % of the monomer mixture was continuously added dropwise to the flask over a period of two hours. After the two hours dropwise addition, 40 g of ethyl acetate was introduced. After the elapse of 8 hours from the start of the dropwise addition, the flask was cooled and 80 g of ethyl acetate was introduced to obtain a nonvolatile content of 40% solution and an acryl type resin having a weight average molecular weight of 185000 and an acid value and a hydroxyl group value both of 0 mgKOH/g (hereinafter referred to as "Acrylic type resin 1"). The acid value and the hydroxyl value were calculated in accordance with the following formulas.

Acid value (mgKOH/g)=[Amount of carboxyl group containing unsaturated monomer charged (wt. %)×0.01×56100]÷[Molecular weight of carboxyl group-containing unsaturated monomer]

Hydroxyl value (mgKOH/g)=[Amount of hydroxyl group containing unsaturated monomer (wt. %)×0.01×56100]÷[Molecular weight of hydroxyl group-containing unsaturated monomer]

SYNTHESIS EXAMPLES 2–15

Acryl type resins were obtained by following the procedure of Synthesis Example 1 while preparing compositions shown in Tables 1 and 2 instead. These experiments will be referred to as Synthesis Examples 2–15.

EXAMPLE 1

A visible light absorbing resin composition was prepared by compounding 250 parts of the acryl type resin of Synthesis Example 1 as a binder resin, 0.1 g of a Dye A (tetraazaporphyrin type dye) represented by the following chemical formula, and 250 g of methylethyl ketone. This resin composition as a base material was applied to a PET film (made by Toyobo K.K. and sold under the product code of "A-4100") having a thickness of 188 microns and having both surfaces treated to facilitate adhesion. The applied layer of the base material was dried at 100° C. for three minutes to form a coating film 10 μm in thickness. The film manufactured by the method described above was rated for stability at room temperature, humidity resistance and heat resistance. The composition and the results are shown in Tables 3 and 5.

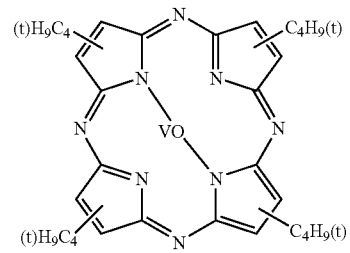

EXAMPLES 2–14

Examples 2–14 were performed by following the procedure of Example 1 while using dipyrazolyl squalilium type dye shown below as Dye B and anthraquinone type dye (product of Abisia K.K. sold under the trademark designation of "WAXOLINE Blue A/AP FW") as Dye C in accordance with Tables 3 and 4. The compositions and the results are shown in Tables 3–6.

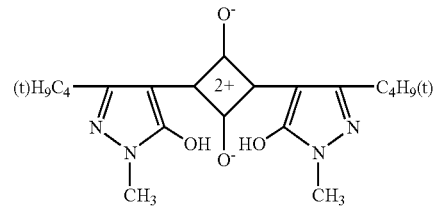

COMPARATIVE EXAMPLES 1–7

In Comparative Examples 1–7, coated films were manufactured by following the procedure of Example 1 while the diluting solvents and the drying conditions were changed as shown in Table 4. They were rated for stability at room temperature, humidity resistance, and heat resistance. The compositions and the results are shown in Tables 7 and 8.

(Method of Evaluation)

(1) Stability at Room Temperature

A sample was left standing at room temperature for 24 hours. The transmittance at the maximum absorption wavelengths of the dye used was measured before and after the standing to find the difference of transmittance before and after the standing. The ability of the dye to retain the absorption property was rated from the change of transmittance of the coating film on the following standard. The difference of transmittance serves as an index which decreases in proportion to an increase in excellence of stability at room temperature. The transmittance, ie the transmittance relative to the light of incidence from the dye-containing coating film layer was measured by the use of a spectrophotometer (the product of Shimadzu Seisakusho K.K. sold under the product code of "UV-3100"). The ability of the dye to retain the absorbing property was evaluated on the three-point scale, wherein ○ denotes less than 1%, Δ for not less than 1% and less than 5%, and X for not less than 5%.

(2) Humidity Resistance

A sample was left standing for 1,000 hours, 1,500 hours, and 2,000 hours in an atmosphere kept at 60° C. and a relative humidity of 95% RH. The transmittance at the maximum absorption wavelengths of the dye used was measured before and after the standing by the use of the same spectrophotometer to find the difference of transmittance before and after the standing. The ability of the dye to retain the absorption property was rated from the change in transmittance of the coating film based on the following standard. The difference of transmittance serves as an index which decreases in proportion to an increase in the excellence of humidity resistance. The adhesiveness of the coating film to the substrate was determined by subjecting a sample having 100 cross-cut (I cm) squares incised therein to a peel test with an adhesive tape as specified in JIS (Japanese Industrial Standard) 5400 (1995 version). The condition of the sample after the peel test was rated based on the following standard.

Ability of dye to retain absorption property rated on the three-point scale, wherein ○ denotes less than 1%, Δ for not less than 1% and less than 5%, and X for not less than 5%.

Adhesiveness to the substrate rated on the two-point scale, wherein ○ denotes absence of abnormality and X occurrence of separation (3) Heat Resistance A sample was left standing for 1,000 hours, 1,500 hours, and 2,000 hours in an atmosphere kept at 80° C. The transmittance at the maximum absorption wavelengths of the dye used was measured before and after the standing by the use of the same spectrophotometer to find the difference of transmittance before and after the standing. The ability of the dye to retain the absorption property was rated from the change in transmittance of the coating film based on the following standard. The difference of transmittance serves as an index which decreases in proportion to an increase in the excellence of humidity resistance. The adhesiveness of the coating film to the substrate was determined by subjecting a sample having 100 cross-cut (I cm) squares incised therein to a peel test with an adhesive tape as specified in JIS (Japanese Industrial Standard) 5400 (1995 version). The condition of the sample after the peel test was rated based on the following standard.

Ability of dye to retain absorption property rated on the three-point scale, wherein ○ denotes less than 1%, Δ for not less than 1% and less than 5%, and X for not less than 5%.

Adhesiveness to the substrate rated on the two-point scale, wherein ○ denotes absence of abnormality and X occurrence of separation

TABLE 1

| | Synthesis examples of acryl type resin | | | | | | |
|---|---|---|---|---|---|---|---|
| | Synthesis Example | | | | | | |
| | 1 | 2 | 3 | 4 | 5 | 6 | 7 |
| MAA | | 0.5 | 4 | 0.5 | | | |
| HEMA | | | | | | | 2 |
| CHMA | 10 | 50 | | | 10 | 10 | 50 |
| IBX | | | 96 | | | | |
| FM108 | | | | 30 | | | |
| MMA | 90 | 49.5 | | 69.5 | 85 | 85 | 48 |
| RUVA93 | | | | | 5 | | |
| Sumiriser-GS | | | | | | 5 | |
| Total | 100 | 100 | 100 | 100 | 100 | 100 | 100 |
| Initiating agent | 0.5 | 0.5 | 0.5 | 0.5 | 0.5 | 0.5 | 0.5 |
| Acid value(mgKOH/g) | 0 | 3.3 | 26.1 | 3.3 | 0 | 0 | 0 |
| Hydroxyl value(mgKOH/g) | 0 | 0 | 0 | 0 | 0 | 0 | 8.6 |
| Solids | 40 | 40.1 | 39.9 | 40 | 39.9 | 40 | 40 |
| MW*1 | 185,000 | 173,000 | 152,000 | 182,000 | 194,000 | 192,000 | 168,000 |
| Acryl type resin | 1 | 2 | 3 | 4 | 5 | 6 | 7 |

MAA = Methacrylic acid,
HEMA = 2-hydroxyethyl methacrylate,
CHMA = cyclohexyl methacrylate,
IBX = isobornyl methacrylate,
FM-108 = perfluorooctylethyl methacrylate (product of Kyoeisha Chemical CO., LTD. "Light Ester FM108"),
MMA = methyl methacrylate,
RUVA93 = ultraviolet light absorbing monomer (product of Otsuka Chemical CO., LTD. "RUVA93"),
Sumiriser-GS = monomer possessing capable of preventing oxidation (product of Sumitomo Chemical CO., LTD. "Sumiriser-GS"),
*1Weight average molecular weight.

TABLE 2

Synthesis Example of acryl type resin

| | \multicolumn{8}{c}{Synthesis Example} |
|---|---|---|---|---|---|---|---|---|
| | 8 | 9 | 10 | 11 | 12 | 13 | 14 | 15 |
| MAA | 0.5 | 5 | 0.5 | 0.5 | | 2 | | 0.5 |
| HEMA | 6 | | 8 | | | | | |
| CHMA | 50 | 50 | 50 | | | 15 | | |
| IBX | | | | 100 | | | | |
| FM108 | | | | | | | | 5 |
| MMA | 43.5 | 45 | 41.5 | 99.5 | | 58 | 20 | 59.5 |
| RUVA93 | | | | | | | | |
| TBMA | | | | | | 25 | 70 | 35 |
| NBMA | | | | | | | 10 | |
| Total | 100 | 100 | 100 | 100 | 100 | 100 | 100 | 100 |
| Initiating agent | 0.5 | 0.5 | 0.5 | 0.5 | 0.5 | 0.1 | 0.7 | 0.5 |
| Acid value(mgKOH/g) | 3.3 | 32.6 | 3.3 | 3.3 | 0 | 13 | 0 | 3.3 |
| Hydroxyl value(mgKOH/g) | 25.9 | 0 | 34.5 | 0 | 0 | 0 | 0 | 0 |
| Solids | 39.9 | 40.1 | 40 | 39.9 | 40.1 | 40 | 39.9 | 39.9 |
| MW*1 | 165,000 | 170,000 | 172,000 | 205,000 | 155,000 | 387,000 | 212,000 | 175,000 |
| Acryl type resin | 8 | 9 | 10 | 11 | 12 | 13 | 14 | 15 |

MAA = methacrylic acid,
HEMA = 2-hydroxyethyl methacrylate,
CHMA = cyclohexyl methacrylate,
IBX = isobornyl methacrylate,
TBMA = tert-butyl methacrylate,
MMA = methyl methacrylate,
NBMA = n-butyl methacrylate,
FM-108 = perfluorooctylethyl methacrylate (product of Kyoeisha Chemical CO., LTD. "Lightester FM108"),
RUVA93 = ultraviolet light absorbing monomer (product of Otsuka Chemical CO., LTD. "RUVA93"),
*1Weight average molecular weight.

TABLE 3

| | | | \multicolumn{7}{c}{Example} |
|---|---|---|---|---|---|---|---|---|---|
| | | | 1 | 2 | 3 | 4 | 5 | 6 | 7 |
| | Dye | A*1 | 0.1 | | | 0.1 | | | 0.1 |
| | | B*2 | | 0.1 | | | 0.1 | 0.1 | |
| | | C*3 | | | 0.1 | | | | |
| Resin composition to form visible light absorbing layer | Acryl type resin | 1 | 250 | | | | | | |
| | | 2 | | 250 | | | | | |
| | | 3 | | | 250 | | | | |
| | | 4 | | | | 250 | | | |
| | | 5 | | | | | 250 | | |
| | | 6 | | | | | | 250 | |
| | | 7 | | | | | | | 250 |
| | Diluting solvent | MEK*4 | 250 | 250 | 250 | 250 | 250 | 250 | 250 |
| | | Toluene*5 | | | | | | | |
| Conditions for forming coating film | Drying temperature(° C.) | | 100 | 100 | 100 | 100 | 100 | 100 | 100 |
| | Drying time | | 3 min. | 3 min. | 3 min. | 3 min. | 3 min. | 3 min. | 3 min. |
| | Thickness* | | 10 | 10 | 10 | 10 | 10 | 10 | 10 |

*1Tetraazaporphyrin type dye
*2Dipyrazolil squarlium type dye
*3Anthraquinone type dye, product of Azisia K.K. WAXOLINE Blue A/AP FW
*4MEK: Methylethyl ketone (boiling point about 80° C.),
*5Toluene (boiling point about 110° C.)
*6Thickness: Thickness of dried film (μm)

TABLE 4

|  |  |  | Example 8 | Example 9 | Example 10 | Example 11 | Example 12 | Example 13 | Example 14 |
|---|---|---|---|---|---|---|---|---|---|
| Dye | | A*1 | 0.1 | | | | | 0.1 | 0.1 |
| | | B*2 | | 0.1 | 0.1 | | 0.1 | | |
| | | C*3 | | | | 0.1 | | | |
| Resin composition to form visible light absorbing layer | Acryl type resin | 1 | | | | | | | |
| | | 2 | | 250 | 250 | | | | |
| | | 3 | | | | | | | |
| | | 4 | | | | | | | |
| | | 5 | | | | | | | |
| | | 6 | | | | | | | |
| | | 7 | | | | | | | |
| | | 8 | 250 | | | | | | |
| | | 9 | | | | | | | |
| | | 10 | | | | | | | |
| | | 11 | | | | | | | |
| | | 12 | | | | | 250 | | |
| | | 13 | | | | | | 250 | |
| | | 14 | | | | | | | 250 |
| | | 15 | | | | | | | 250 |
| | Diluting solvent | MEK*4 | 250 | 250 | | 250 | 250 | 250 | 250 |
| | | Toluene*5 | | | 250 | | | | |
| Conditions for forming coating film | Drying temp. (° C.) | | 100 | 100 | 100 | 100 | 100 | 100 | 100 |
| | Drying time | | 3 min. | 30 sec. | 30 sec. | 3 min. | 3 min. | 3 min. | 3 min. |
| | Thickness*6 | | 10 | 10 | 10 | 10 | 10 | 10 | 10 |

*1 Tetraazaporphyrin type dye,
*2 Dipyrazolylsqualium type dye
*3 Anthraquinone type dye, product of Azisia K.K. "WAXOLIN Blue A/AP FW
*4 MEK: Methylethyl ketone (boiling point about 80° C.),
*5 Toluene (boiling point about 110° C.)
*6 Thickness: Thickness of dried film (μm)

TABLE 5

|  |  |  | Example 1 | Example 2 | Example 3 | Example 4 | Example 5 | Example 6 | Example 7 |
|---|---|---|---|---|---|---|---|---|---|
| Dye | | A*1 | 0.1 | | | 0.1 | | 0.1 | |
| | | B*2 | | 0.1 | | | 0.1 | 0.1 | |
| | | C*3 | | | 0.1 | | | | |
| Results of evaluation | Stability at room temperature | [A] 24 hours | ○ | ○ | ○ | ○ | ○ | ○ | ○ |
| | Humidity resistance | [A] 1,000 hours | ○ | ○ | ○ | ○ | ○ | ○ | ○ |
| | | [B] 1,000 hours | ○ | ○ | ○ | ○ | ○ | ○ | ○ |
| | | [A] 1,500 hours | ○ | ○ | ○ | ○ | ○ | ○ | ○ |
| | | [B] 1,500 hours | ○ | ○ | ○ | ○ | ○ | ○ | ○ |
| | | [A] 2,000 hours | Δ | ○ | ○ | ○ | ○ | ○ | ○ |
| | | [B] 2,000 hours | ○ | ○ | ○ | ○ | ○ | ○ | ○ |
| | Heat resistance | [A] 1,000 hours | ○ | ○ | ○ | ○ | ○ | ○ | ○ |
| | | [B] 1,000 hours | ○ | ○ | ○ | ○ | ○ | ○ | ○ |
| | | [A] 1,500 hours | ○ | ○ | ○ | ○ | ○ | ○ | ○ |
| | | [B] 1,500 hours | ○ | ○ | ○ | ○ | ○ | ○ | ○ |
| | | [A] 2,000 hours | Δ | ○ | ○ | ○ | ○ | ○ | ○ |
| | | [B] 2,000 hours | ○ | ○ | ○ | ○ | ○ | ○ | ○ |

*1 Tetraazaporphyrin type dye
*2 Dipyrazolylsqualium type dye
*3 Anthraquinone type dye, product of Azisia K.K. "WAXOLIN Blue A/AP FW
[A] = Ability to absorb dye after prescribed hours in the Table.
[B] = Adhesiveness after prescribed hours in the Table.

TABLE 6

|  |  |  | Example | | | | | | |
|---|---|---|---|---|---|---|---|---|---|
|  |  |  | 8 | 9 | 10 | 11 | 12 | 13 | 14 |
| Dye |  | A*1 |  |  |  |  |  | 0.1 | 0.1 |
|  |  | B*2 | 0.1 | 0.1 | 0.1 | 0.1 | 0.1 |  |  |
|  |  | C*3 |  |  |  |  |  |  |  |
| Results of evaluation | Stability at room temperature | [A] 24 hours | ○ | ○ | ○ | ○ | ○ | ○ | ○ |
|  | Humidity resistance | [A] 1,000 hours | ○ | ○ | ○ | ○ | ○ | ○ | ○ |
|  |  | [B] 1,000 hours | ○ | ○ | ○ | ○ | ○ | ○ | ○ |
|  |  | [A] 1,500 hours | ○ | ○ | ○ | ○ | ○ | ○ | ○ |
|  |  | [B] 1,500 hours | ○ | ○ | ○ | ○ | ○ | ○ | ○ |
|  |  | [A] 2,000 hours | ○ | ○ | ○ | ○ | ○ | ○ | ○ |
|  |  | [B] 2,000 hours | ○ | ○ | ○ | ○ | ○ | ○ | ○ |
|  | Heat resistance | [A] 1,000 hours | ○ | ○ | ○ | ○ | ○ | ○ | ○ |
|  |  | [B] 1,000 hours | ○ | ○ | ○ | ○ | ○ | ○ | ○ |
|  |  | [A] 1,500 hours | ○ | ○ | ○ | ○ | ○ | ○ | ○ |
|  |  | [B] 1,500 hours | ○ | ○ | ○ | ○ | ○ | ○ | ○ |
|  |  | [A] 2,000 hours | ○ | ○ | ○ | ○ | ○ | ○ | ○ |
|  |  | [B] 2,000 hours | ○ | ○ | ○ | ○ | ○ | ○ | ○ |

*1 Tetraazaporphyrin type dye
*2 Dipyrazolylsqualium type dye
*3 Anthraquinone type dye, product of Azisia K.K. "WAXOLIN Blue A/AP FW"
[A] = Ability to absorb dye after prescribed hours in the Table.
[B] = Adhesiveness after prescribed hours in the Table.

TABLE 7

|  |  |  | ComparativeExample | | | | | | |
|---|---|---|---|---|---|---|---|---|---|
|  |  |  | 1 | 2 | 3 | 4 | 5 | 6 | 7 |
| Dye |  | A*1 |  |  |  |  | 0.1 | 0.1 | 0.1 |
|  |  | B*2 | 0.1 | 0.1 | 0.1 | 0.1 |  |  |  |
|  |  | C*3 |  |  |  |  |  |  |  |
| Resin composition to form visible light absorbing layer | Acryl type resin | 1 |  |  |  |  |  |  |  |
|  |  | 2 |  |  |  |  |  |  |  |
|  |  | 3 |  |  |  |  |  |  |  |
|  |  | 4 |  |  |  |  |  |  |  |
|  |  | 5 |  |  |  |  |  |  |  |
|  |  | 6 |  |  |  |  |  |  |  |
|  |  | 7 |  |  |  |  |  |  |  |
|  |  | 8 |  |  |  |  |  |  |  |
|  |  | 9 | 250 |  |  |  |  |  |  |
|  |  | 10 |  | 250 | 250 | 250 |  |  |  |
|  |  | 11 |  |  |  |  | 250 | 250 | 250 |
|  | Diluting solvent | Methyl ethyl ketone | 250 | 250 | 250 |  | 250 | 250 |  |
|  |  | Toluene |  |  |  | 250 |  |  | 250 |
| Conditions for forming coating film | Drying temperature |  | 100° C. | 100° C. | 100° C. | 100° C. | 100° C. | 100° C. | 100° C. |
|  | Drying time |  | 3 min. | 3 min. | 30 sec. | 30 sec. | 3 min. | 30 sec. | 30 sec. |
|  | Thickness of dried film |  | 10 μm | 10 μm | 10 μm | 10 μm | 10 μm | 10 μm | 10 μm |

*1 Tetraazaporphyrin type dye
*2 Dipyrazolylsqualilium type dye
*3 Anthraquinone type dye, product of Abisia K.K. "WAXOLINE Blue A/AP FW"

TABLE 8

|  |  |  | Comparative Example | | | | | | |
|---|---|---|---|---|---|---|---|---|---|
|  |  |  | 1 | 2 | 3 | 4 | 5 | 6 | 7 |
| Dye |  | A*¹ |  |  |  |  | 0.1 | 0.1 | 0.1 |
|  |  | B*² | 0.1 | 0.1 | 0.1 | 0.1 |  |  |  |
|  |  | C*³ |  |  |  |  |  |  |  |
| Results of evaluation | Stability at room temperature | [A] 24 hours | Δ | Δ | X | X | Δ | X | X |
|  | Humidity resistance | [A] 1,000 hours | X | X | X | X | X | X | X |
|  |  | [B] 1,000 hours | ○ | ○ | Δ | Δ | X | X | X |
|  |  | [A] 1,500 hours | X | X | X | X | stop | stop | stop |
|  |  | [B] 1,500 hours | Δ | Δ | X | X | stop | stop | stop |
|  |  | [A] 2,000 hours | X | X | stop | stop | stop | stop | stop |
|  |  | [B] 2,000 hours | X | X | stop | stop | stop | stop | stop |
|  | Heat resistance | [A] 1,000 hours | X | X | X | X | X | X | X |
|  |  | [B] 1,000 hours | ○ | ○ | ○ | ○ | ○ | ○ | ○ |
|  |  | [A] 1,500 hours | X | X | X | X | X | X | X |
|  |  | [B] 1,500 hours | Δ | Δ | Δ | Δ | Δ | Δ | Δ |
|  |  | [A] 2,000 hours | X | X | X | X | X | X | X |
|  |  | [B] 2,000 hours | Δ | Δ | Δ | Δ | X | X | X |

*¹Tetraazaporphyrin type dye
*²Dipyrazolylsquailium type dye
*³Anthraquinone type dye, product of Abisia K.K. "WAXOLINE Blue A/AP FW"
[A] = Ability to absorb dye after prescribed hours in the Table.
[B] = Adhesiveness after prescribed hours in the Table.

(Results)

(1) It is clear from the results of Examples 1–14 that when the acryl type resins having acid value in the range of 0–30 mgKOH/g and hydroxyl values in the range of 0–30 mgKOH/g and obtained by polymerizing monomer mixtures containing monomers represented by the formula (1) mentioned above and/or 5–100 wt. % of fluorine atom-containing unsaturated monomers were used as binder resins, the tetraazaporphyrin type dye, dipyrazolyl squalium type dye and the anthraquinone type dye invariably manifested excellent heat resistance, humidity resistance and stability at room temperature.

(2) It is clear from Examples 5 and 6 that when the acryl type resins obtained by copolymerizing an ultraviolet light absorbing monomer and a monomer capable of preventing oxidation were used, the humidity resistance and the heat resistance were improved.

(3) It is clear from comparing Example 2 and Example 9 that even when the drying time was shortened from three minutes to 30 seconds, the heat resistance, the humidity resistance, and the stability at room temperature were not degraded and the dye was prevented from deterioration for a long time.

(4) It is clear from comparing Example 2 and example 10, even when toluene having a boiling point of 110° C. was used in the place of methylethyl ketone having a boiling point of 80° C. and the drying time was shortened from three minutes to 30 seconds, the heat resistance, the humidity resistance, and the stability at room temperature were not degraded and the dye was prevented from deterioration for a long time.

(5) In Comparative Examples 1 and 2, the stability at room temperature, the humidity resistance, and the heat resistance were degraded because the acryl type resin used has acid value or hydroxyl values deviated from the ranges specified by this invention.

(6) It is clear from comparing Comparative Example 1 and Comparative Example 3 that the humidity resistance and the stability at room temperature were further degraded when the drying time was shortened from three minutes to 30 seconds.

(7) It is clear from comparing Comparative Example 2 and Comparative Example 4 that the humidity resistance and the stability at room temperature were further degraded when toluene having a boiling point of 110° C. was used in the place of methylethyl ketone having a boiling point of 80° C. and the drying time was shortened from three minutes to 30 seconds.

(8) In Comparative examples 5 and 6, though the acid value and the hydroxyl values both fell in the range of 0–30 mgKOH/g, the monomer represented by the formula (1) and/or the fluorine atom-containing unsaturated monomer were not contained in amounts falling in the range of 5–100 wt. %. When these resins were used as binder resins, the heat resistance, the humidity resistance, and the stability at room temperature were invariably lower than when the acryl type resin contemplated by this invention was used, no matter whether the drying time was three minutes or 30 seconds.

(9) In Comparative Example 7, toluene having a boiling point of 110° C. was used and the drying time was shortened to 30 seconds. The heat resistance, the humidity resistance, and the stability at room temperature were invariably lower than when the acryl type resin contemplated by this invention was used.

The invention claimed is:

1. A resin composition comprising an acrylic resin obtained by polymerizing a monomer mixture containing 5–100 wt. % of a monomer represented by the following formula (1) and/or a fluorine atom-containing unsaturated monomer and having an acid value in the range of 0–30 mgKOH/g and a hydroxyl value in the range of 0–30 mgKOH/g, and a dye having the maximum absorption at a wavelength in the range of 380–780 nm:

$$CH_2=CR-COOX \qquad (1),$$

wherein R denotes a hydrogen atom or a methyl group and X denotes a hydrocarbon group of 4–25 carbon atoms.

2. An optical filter comprising a layer formed of the resin composition set forth in claim 1 on a transparent substrate layer.

3. An optical filter according to claim 2, further comprising a dye having the maximum absorption at a wavelength in the range of 780–1,200 nm.

4. An optical filter according to claim 3, wherein the dye having the maximum absorption at a wavelength in the range of 780–1,200 nm is contained in said resin composition.

5. A plasma display using an optical filter set forth in claim 4.

6. A plasma display using an optical filter set forth in claim 3.

7. A plasma display using an optical filter set forth in claim 2.

8. A resin composition according to claim 1, wherein the acrylic resin is 50–99.9995 wt % of the resin composition based on 100 wt % of the composition reduced to an involatile form.

9. A resin composition according to claim 1, wherein the acrylic resin is 60–99.9985 wt % of the resin composition based on 100 wt % of the composition reduced to an involatile form.

10. A resin composition according to claim 1, wherein the acrylic resin is 70–99.9985 wt % of the resin composition based on 100 wt % of the composition reduced to an involatile form.

11. A resin composition according to claim 1, wherein the acrylic resin is obtained by polymerizing a fluorine atom-containing unsaturated monomer.

12. A resin composition according to claim 1, wherein the acrylic resin has a glass transition temperature in the range of −30 to 180° C.

* * * * *